(12) United States Patent
Bigot

(10) Patent No.: US 6,262,308 B1
(45) Date of Patent: Jul. 17, 2001

(54) PROCESS FOR THE PREPARATION OF RACEMIC SERTRALINE

(75) Inventor: Patrick Bigot, Lyons (FR)

(73) Assignee: Catalys, Lyons (FR)

( * ) Notice: Subject to any disclaimer, the term of this patent is extended or adjusted under 35 U.S.C. 154(b) by 0 days.

(21) Appl. No.: 09/280,673

(22) Filed: Mar. 29, 1999

(30) Foreign Application Priority Data

Apr. 1, 1998 (FR) .................................. 98 04270

(51) Int. Cl.[7] ................................. C07C 211/38

(52) U.S. Cl. .................. 564/428; 564/192; 564/217; 564/218; 564/221; 564/222; 564/414

(58) Field of Search ................... 564/217, 218, 564/221, 222, 192, 428, 414

(56) References Cited

U.S. PATENT DOCUMENTS 5,442,116 * 8/1995 Welch et al. ..................... 564/222
5,463,126 * 10/1995 Williams ........................... 564/222

FOREIGN PATENT DOCUMENTS

| 0 030 081 A1 | 6/1981 | (EP) . |
| 0 346 226 A1 | 12/1989 | (EP) . |
| WO 93/01161 | 1/1993 | (WO) . |
| WO 93/01162 | 1/1993 | (WO) . |

OTHER PUBLICATIONS

Repinskaya, Sib. Khim. Zh. (1993) 73–76 (Chemical Abstracts, 120, 106497)—Abstract Only.
Welch et al, J. Labelled. Comp. Radiopharm., vol. XXIV, No. 8, pp 987–992, 1987.*
Corey et al, Tetrahedron Lett., vol. 35, No. 35, pp 5373–5376, 1994.*

* cited by examiner

Primary Examiner—Shailendra Kumar
(74) Attorney, Agent, or Firm—Oliff & Berridge, PLC

(57) ABSTRACT

The invention relates to a process for preparing cis-N-methyl-4-(3,4-dichlorophenyl)-1,2,3,4-tetrahydro-1-naphthylamine, or racemic sertraline, corresponding to formula (I)

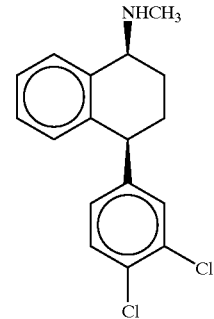

(I)

in salt form, starting with 4-(3,4-dichlorophenyl)tetralone of formula (II)

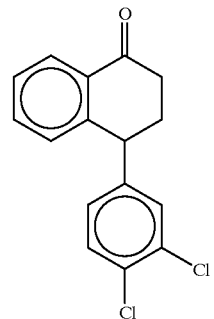

(II)

according to which (a) the 4-(3,4-dichlorophenyl) tetralone of formula (II) is reacted with N-methylformamide in the presence of formic acid, (b) the reaction medium obtained according to (a) is treated with a base, and (c) the racemic sertraline salt is separated out by selective crystallization with an acid. The invention also relates to N-methylformamide-4-(3, 4-dichlorophenyl)-1,2,3,4-tetrahydro-1-naphthylamine and to its use to obtain racemic sertraline.

10 Claims, No Drawings

PROCESS FOR THE PREPARATION OF RACEMIC SERTRALINE

The present invention relates to a process for the preparation of racemic cis-N-methyl-4-(3,4-dichlorophenyl)-1,2,3,4-tetrahydro-1-naphthylamine, also known as racemic sertraline, corresponding to formula (I) below:

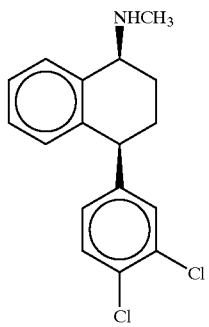

(I)

isolated in salt form.

The S,S enantiomer of sertraline, in the form of the hydrochloride salt, corresponding to the following formula:

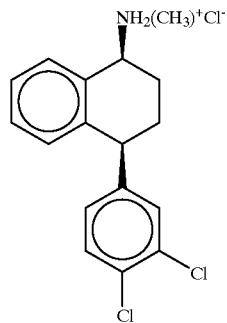

has a therapeutic application in the treatment of depression and associated problems, as described, for example, in document EP-0,030,081.

At the present time, the racemic salt from which the abovementioned pharmaceutically active salt is isolated is obtained from 4-(3,4-dichlorophenyl)tetralone of formula (II) below:

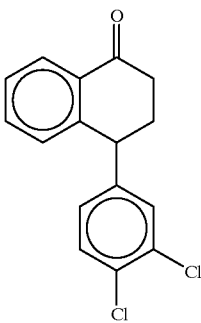

(II)

In accordance with the synthesis of compound (I) in salt form described in the said document EP-0,030,081, 4-(3,4-dichlorophenyl)tetralone of formula (II) is reacted with anhydrous methylamine, in the presence of a dehydrating reagent, a hydrogenation reaction of the condensation product obtained is carried out over palladium on charcoal and the salt of the racemic cis-N-methyl-4-(3,4-dichlorophenyl)-1,2,3,4-tetrahydro-1-naphthylamine is separated out by selective crystallization.

This process has several drawbacks. Firstly, it uses dangerous reagents such as anhydrous methylamine, titanium tetrachloride and gaseous hydrogen chloride. Next, during this process, partial hydrogenolysis of the chloro substituents on the phenyl ring takes place, leading to the formation of monochloro sertraline compounds.

The Applicant has developed a process for obtaining racemic sertraline from 4-(3,4-dichlorophenyl)tetralone which avoids the problems encountered above.

The subject of the present invention is a process for the preparation, in two steps, of racemic cis-N-methyl-4-(3,4-dichlorophenyl)-1,2,3,4-tetrahydro-1-naphthylamine (or racemic sertraline) corresponding to formula (I), in salt form, the said process comprising the steps according to which:

(a) 4-(3,4-dichlorophenyl)tetralone of formula (II) described above is reacted with N-methylformamide in the presence of formic acid, (b) the reaction medium obtained according to (a) is treated with a base, and (c) the salt of the racemic cis-N-methyl-4-(3,4-dichlorophenyl)-1,2,3,4-tetrahydro-1-naphthylamine is separated out by selective crystallization with an acid.

The process of the invention is very advantageous since, starting with the salt which it gives, sertraline can be obtained in a single crystallization step, in virtually pure form.

Preferably, in step (a), the 4-(3,4-dichlorophenyl)tetralone of formula (II) is in a mixture with 4-(2,3-dichlorophenyl)tetralone of formula (III) described below.

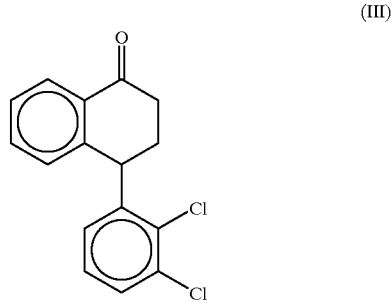

(III)

This variant of the process of the invention is particularly advantageous for the following reasons:

the pure 4-(3,4-dichlorophenyl)tetralone of formula (II) is obtained in five steps in accordance with the process described in the abovementioned document EP-0,030,081; its synthesis in only one step is also described in EP-0,346,226, by reaction of α-naphthol with ortho-dichlorobenzene in the presence of a Lewis acid such as aluminum chloride; to obtain the tetralone in essentially pure form, according to this second route, two crystallization steps are necessary; the authors of the article Repinskaya, Sib. Khim. Zh. (1993) 73–76 (Chemical Abstracts, 120, 106497) have demonstrated that, under the conditions for obtaining tetralone in a single step (EP-0,346,226), a mixture of the isomers 4-(3,4-dichlorophenyl)tetralone of formula (II) and 4-(2,3-dichlorophenyl)tetralone of formula (III) is in fact obtained in a (II)/(III) ratio of 4.9/1; the variant of the process of the invention proposes to react the mixture of tetralones (II) and (III) directly after reaction of α-naphthol with ortho-dichlorobenzene, without prior purification of the tetralone (II);

the fact that 4-(3,4-dichlorophenyl)tetralone of formula (II) is available as a mixture with 4-(2,3-dichlorophenyl)tetralone of formula (III) does not place a burden on the step for separating out the salt to be obtained.

In the context of the invention, preferred implementations of the process were determined; these are outlined below.

For step (a) the following characteristics can be selected alone; they will advantageously be chosen in combination.

Step (a) is carried out at a temperature ranging from 150° C. to 220° C., preferably ranging from 180° C. to 200° C.

The N-methylformamide is present in a molar ratio ranging from 1.1 to 5 relative to the mixture of the 4-(dichlorophenyl)tetralones of formulae (II) and (III), respectively, and preferably ranging from 2.5 to 3.

Formic acid, which acts as a reducing agent in this reaction, is advantageously introduced in fractions of 10% of the total amount to be added. The latter amount preferably represents a molar ratio ranging from 1.1 to 5, and better still ranging from 1.1 to 2, relative to the abovementioned mixture.

When the 4-(3,4-dichlorophenyl)tetralone of formula (II) is in a mixture with 4-(2,3-dichlorophenyl)tetralone of formula (III), the weight proportion of the 4-(3,4-dichlorophenyl)tetralone in this mixture is at least 80%, that of the 4-(2,3-dichlorophenyl) tetralone being not more than 20%. The mixture is very advantageously obtained by reaction of α-naphthol with ortho-dichlorobenzene, in the presence of aluminum chloride, preferably under the conditions described in document EP-0,346,226. According to the indications described in Chemical Abstracts 120, 106497, the mixture thus obtained contains about 82% of compound of formula (II) and 18% of compound of formula (III).

Similarly, for step (b), it is desirable to select the following characteristics.

The base used in step (b) to deformylate the N-methylformamide-4-(dichlorophenyl)-1,2,3,4-tetrahydro-1-naphthylamines obtained in step (a) preferably consists of an alkali metal hydroxide, such as potassium hydroxide, sodium hydroxide or lithium hydroxide, the former being preferred.

This base can be used in pure form or as an aqueous solution.

Step (b) is preferentially carried out in a hydroxylated solvent, such as an alcoholic solvent. This advantageously consists of a $C_1$–$C_8$ alcohol, and preferably consists of 1-butanol. Favorable conditions for the deformylation are a reflux temperature of the solvent and a reaction time of at least three hours.

At the end of step (b), the resulting alkali metal formates are dissolved in the aqueous phase, and the racemic sertraline salt is obtained, in step (c), by selective crystallization by treating the organic phase with an acid, such as a halo acid, preferably hydrochloric acid, an alkylsulfonic acid, preferably methanesulfonic acid, or an arylsulfonic acid, preferably para-toluenesulfonic acid.

The precipitation, isolation and purification of the salt obtained in step (c) are carried out according to standard techniques which are well known to those skilled in the art. According to the preferred acid used, a salt chosen from the methanesulfonate, the para-toluenesulfonate and the hydrochloride is thus obtained.

Starting with the racemic sertraline salt, a person skilled in the art will make use of known methods for separating enantiomers in order to obtain the S,S enantiomer of sertraline hydrochloride, which has therapeutic properties. As an example, this separation can be carried out by crystallization of the salt of an optically active acid or by chromatography on a chiral phase followed by salification with hydrochloric acid.

Another subject of the invention is the compound N-methylformamide-4-(3,4-dichlorophenyl)-1,2,3,4-tetrahydro-1-naphthylamine, which corresponds to formula (IV) below.

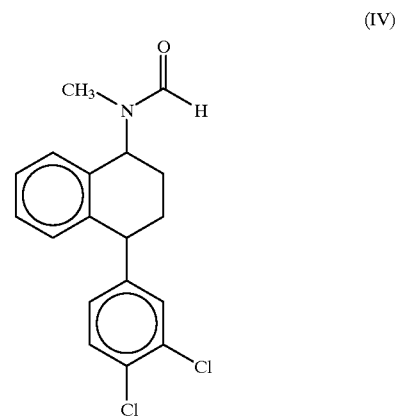

(IV)

This compound is an intermediate in the synthesis of sertraline. It can be obtained by reaction of a mixture of 4-(3,4-dichlorophenyl)tetralone of formula (II) and 4-(2,3-dichlorophenyl)tetralone of formula (III) with N-methylformamide in the presence of formic acid.

The invention also relates to the use of N-methylformamide-4-(3,4-dichlorophenyl)-1,2,3,4-tetrahydro-1-naphthylamine to obtain racemic cis-N-methyl-4-(3,4-dichlorophenyl)-1,2,3,4-tetrahydro-1-naphthylamine.

The characteristics and advantages of the invention are illustrated with the support of Examples 1 to 6 below. In Examples 1 to 4, the synthesis of the racemic sertraline salt is carried out starting with a mixture of the compounds of formulae (II) and (III), whereas in Examples 5 and 6, the synthesis is carried out starting with the compound of formula (II) alone.

EXAMPLE 1

Production of the Mixture of Compounds of Formulae (V) and (VI) After Steps (a) and (b)

A suspension of 86.5 g (0.6 mol) of α-naphthol in 340 ml of ortho-dichlorobenzene is reacted with 160 g of aluminum chloride for 2 hours at 120° C. The solution obtained is hydrolyzed with 300 ml of water at 80° C. The lower, organic phase is separated out and the excess ortho-dichlorobenzene is concentrated under a vacuum of 20 mm Hg. The residue of about 215 g is dissolved in 148 g of N-methylformamide and heated at 195–200° C. for 5 hours with fractional addition of 25 g of formic acid during this period. The excess N-methylformamide is stripped off by atmospheric distillation until a mass temperature of 220° C. is obtained.

The reaction mixture, cooled to 100° C., is diluted with 200 ml of 1-butanol at 100° C. 110 g of potassium hydroxide are added over 1 hour with stirring and the medium is maintained at reflux for 4 hours.

EXAMPLE 2
Step (c) by Treatment with Methanesulfonic Acid

The mixture of amines obtained as a butanolic solution according to Example 1 is salified with 95 g of aqueous 70% methanesulfonic acid solution.

The precipitate formed is filtered off, redissolved in 400 ml of refluxing methanol, treated with 1 g of decolorizing active charcoal, filtered and crystallized between 0° C. and 20° C. to give, after filtration and drying, 51.8 g of racemic cis-N-methyl-(3,4-dichlorophenyl)-1,2,3,4-tetrahydro-1-naphthylamine methanesulfonate with a melting point of 225° C. and an HPLC purity of 99.7%.

The stoichiometric yield is 21.5% relative to the starting α-naphthol.

EXAMPLE 3
Step (c) by Treatment with Para-toluenesulfonic Acid

The mixture of amines obtained as a butanolic solution according to Example 1 is salified with 114 g of para-toluenesulfonic acid monohydrate at 20° C. The precipitate formed is filtered off and then redissolved in 800 ml of refluxing methanol, treated with 1 g of decolorizing active charcoal, filtered and crystallized at 20° C. to give, after drying, 65.5 g of racemic cis-N-methyl-(3,4-dichlorophenyl)-1,2,3,4-tetrahydro-1-naphthylamine para-toluenesulfonate with a melting point of 280° C. and an HPLC purity of 97%.

The stoichiometric yield is 22% relative to the starting α-naphthol.

EXAMPLE 4
Step (c) by Treatment with Hydrochloric Acid

The mixture of amines obtained as a butanolic solution according to Example 1 is salified with 70 ml of concentrated hydrochloric acid at 20° C. The precipitate formed is filtered off and washed with 50 ml of 1-butanol to give 62.1 g of racemic cis-N-methyl-(3,4-dichlorophenyl)-1,2,3,4-tetrahydro-1-naphthylamine hydrochloride with a melting point of 275–280° C., containing, by HPLC, 3% of racemic cis-N-methyl-(2,3-dichlorophenyl)-1,2,3,4-tetrahydro-1-naphthylamine isomer. By dissolution of this mixture in 620 ml of refluxing ethanol and crystallization at 20° C., a product is obtained containing 98.5% of 3,4-isomer and 1% of 2,3-isomer. An additional recrystallization under the same conditions gives 48 g of racemic cis-N-methyl-(3,4-dichlorophenyl)-1,2,3,4-tetrahydro-1-naphthylamine hydrochloride with a melting point of 285–290° C. and an HPLC purity of 99.5%. The stoichiometric yield is 23.3% relative to the starting α-naphthol.

EXAMPLE 5
Production of the Compound of Formula (V) after Steps (a) and (b)

58.2 g (0.2 mol) of 4-(3,4-dichlorophenyl)tetralone and 49 ml of N-methylformamide are heated at 200° C., with addition of 10 ml of formic acid, for 4 hours.

The mixture is cooled and diluted with 80 ml of 1-butanol and 80 ml of water. The butanolic phase is separated out and then concentrated under vacuum to give 77 g of a yellow oil. An aliquot portion of this oil is crystallized in 40 ml of ethanol at 0° C. for 2 days to give, after filtration and drying, 5.2 g of cream-white crystals (melting point 128° C.) of cis-N-[4-(3,4-dichlorophenyl)-1,2,3,4-tetrahydro-1-naphthyl]-N-methylformamide. This is equivalent to a yield of 48% relative to the starting 4-(3,4-dichlorophenyl) tetralone.

EXAMPLE 6
Step (c) by Treatment with Hydrochloric Acid

The butanolic phase obtained according to Example 5 is reacted with 36 g of refluxing potassium hydroxide for 2 hours. After cooling, the mixture is treated with 100 ml of water and the upper, organic phase is separated out. Addition of 30 ml of concentrated hydrochloric acid to this phase produces a white precipitate which is filtered off and dried to give 28.4 g of N-methyl-4-(3,4-dichlorophenyl)-1,2,3,4-tetrahydro-1-naphthylamine hydrochloride with an HPLC purity of 98% of cis form and 2% of trans form, i.e. a yield of 41.4% relative to the starting 4-(3,4-dichlorophenyl) tetralone.

What is claimed is:

1. Process for the preparation of racemic cis-N-methyl-4-(3,4-dichlorophenyl)-1,2,3,4-tetrahydro-1-naphthylamine corresponding to formula (I)

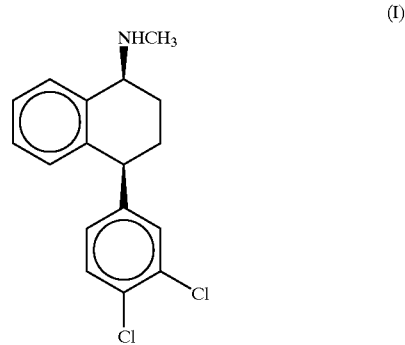

(I)

in salt form, starting with 4-(3,4-dichlorophenyl)tetralone of formula (II)

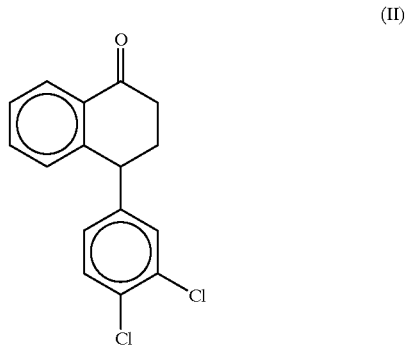

(II)

characterized in that it comprises the steps according to which (a) 4-(3,4-dichlorophenyl)tetralone of formula (II) is reacted with N-methylformamide in the presence of formic acid, (b) the reaction medium obtained according to (a) is treated with a base, and (c) the salt of racemic cis-N-methyl-4-(3,4-dichlorophenyl)-1,2,3,4-tetrahydro-1-naphthylamine is separated out by selective crystallization with an acid.

2. Process according to claim 1, characterized in that, in step (a), the 4-(3,4-dichlorophenyl)tetralone of formula (II) is in a mixture with 4-(2,3-dichlorophenyl)tetralone of formula (III)

(III)

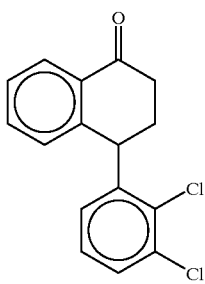

to give, as an intermediate compound, N-methylformamide-4-(3,4-dichlorophenyl)-1,2,3,4-tetrahydro-1-naphthylamine of formula (IV):

(IV)

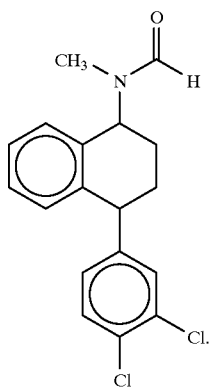

3. Process according to claim 1, characterized in that step (a) is carried out at a temperature ranging from 150° C. to 220° C.

4. Process according to claim 2, characterized in that, in the mixture according to step (a), the weight proportion of the 4-(3,4-dichlorophenyl)tetralone is at least 80%, that of the 4-(2,3-dichlorophenyl)tetralone being not more than 20%.

5. Process according to claim 4, characterized in that the mixture is obtained by reaction of α-naphthol with ortho-dichlorobenzene, in the presence of aluminum chloride.

6. Process according to claim 1, characterized in that step (b) is carried out in a $C_1$–$C_8$ alcoholic solvent maintained at reflux.

7. Process according to claim 6, characterized in that the base is potassium hydroxide and the solvent is 1-butanol.

8. Process according to claim 1, characterized in that, according to step (c), the racemic cis-N-methyl-4-(3,4-dichlorophenyl)-1,2,3,4-tetrahydro-1-naphthylamine is obtained by selective crystallization with an acid chosen from methanesulfonic acid, para-toluenesulfonic acid and hydrochloric acid.

9. Process according to claim 2, characterized in that step (a) is carried out at a temperature ranging from 150° C. to 220° C.

10. Process for the preparation of N-methylformamide-4-(3,4-dichlorophenyl)-2,3,4-tetrahydro-1-naphthylamine of formula (IV), (IV)

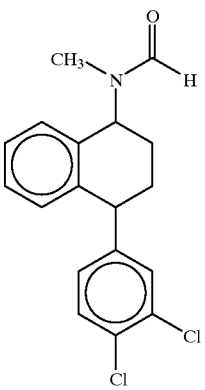

comprising reacting a mixture of 4-(3,4-dichlorophenyl) tetralone of formula (II), (II)

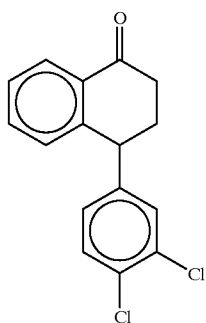

and 4-(2,3-dichlorophenyl)tetralone of formula (III), (III)

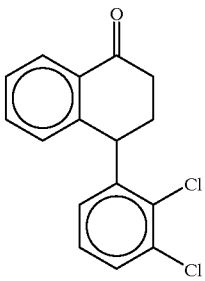

with N-methylformamide in the presence of formic acid.

* * * * *